(12) United States Patent
Zhang et al.

(10) Patent No.: US 11,259,721 B2
(45) Date of Patent: Mar. 1, 2022

(54) METHOD AND DEVICE FOR DETECTING CONCENTRATION OF TOTAL HEMOGLOBIN IN BLOOD

(71) Applicant: BOE Technology Group Co., Ltd., Beijing (CN)

(72) Inventors: Xun Zhang, Beijing (CN); Guangfei Li, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 348 days.

(21) Appl. No.: 16/439,011

(22) Filed: Jun. 12, 2019

(65) Prior Publication Data

US 2020/0093409 A1   Mar. 26, 2020

(30) Foreign Application Priority Data

Sep. 20, 2018 (CN) .......................... 201811099154.5

(51) Int. Cl.
*A61B 5/1455* (2006.01)

(52) U.S. Cl.
CPC .............................. *A61B 5/14551* (2013.01)

(58) Field of Classification Search
CPC . A61B 5/0059; A61B 5/1455; A61B 5/14551; A61B 5/14552; A61B 5/02416; A61B 5/0205; A61B 5/72; A61B 5/7271
See application file for complete search history.

(56) References Cited

U.S. PATENT DOCUMENTS 5,101,825 A * 4/1992 Gravenstein ....... A61B 5/14551
600/326
5,782,756 A * 7/1998 Mannheimer ...... A61B 5/14542
600/322

* cited by examiner

*Primary Examiner* — Chu Chuan Liu
(74) *Attorney, Agent, or Firm* — Arent Fox LLP; Michael Fainberg

(57) ABSTRACT

Disclosed are a method and device for detecting the concentration of total hemoglobin in blood. A differential path factor corresponding to a subject is determined according to a physiological parameter of the subject and a predetermined table of a corresponding relation between the physiological parameter and the differential path factor.

10 Claims, 3 Drawing Sheets

METHOD AND DEVICE FOR DETECTING CONCENTRATION OF TOTAL HEMOGLOBIN IN BLOOD

CROSS-REFERENCE TO RELATED APPLICATION

This application claims priority of Chinese Patent Application No. 201811099154.5, filed on Sep. 20, 2018, which is hereby incorporated by reference in its entirety.

FIELD

The present disclosure relates to the technical field of detection and in particular relates to a method and device for detecting the concentration of total hemoglobin in blood.

BACKGROUND

At present, the measurement for the concentration of total hemoglobin in blood of a human body is performed based on in-vitro analysis for the blood of a subject. Generally, a blood sample is acquired and is then measured so that the concentration of the total hemoglobin is determined.

SUMMARY

Some embodiments of the present disclosure provide the method for detecting the concentration of total hemoglobin in blood, including:

determining a differential path factor corresponding to a subject according to a physiological parameter of the subject and a predetermined table of a corresponding relation between the physiological parameter and the differential path factor, wherein a differential path factor is a difference of a path factor corresponding to a maximum value of a photoplethysmography signal and a path factor corresponding to a minimum value of the photoplethysmography signal;

acquiring a first photoplethysmography signal of the subject under an irradiation of light with a first wavelength and a second photoplethysmography signal of the subject under an irradiation of light with a second wavelength, wherein the first wavelength is different from the second wavelength; and determining the concentration of the total hemoglobin in the blood of the subject according to the first photoplethysmography signal, the second photoplethysmography signal and determined differential path factor.

Alternatively, in some embodiments of the present disclosure, determining the concentration of the total hemoglobin in the blood of the subject includes:

determining a first absorbancy generated when an artery of the subject pulsates under the irradiation of the light with the first wavelength according to the maximum value and the minimum value of the first photoplethysmography signal;

determining a second absorbancy generated when the artery of the subject pulsates under the irradiation of the light with the second wavelength according to the maximum value and the minimum value of the second photoplethysmography signal; and determining the concentration of the total hemoglobin according to the first absorbancy, the second absorbancy and the determined differential path factor.

Alternatively, in some embodiments of the present disclosure, acquiring the first photoplethysmography signal of the subject under the irradiation of the light with the first wavelength and the second photoplethysmography signal of the subject under the irradiation of the light with the second wavelength specifically includes:

acquiring the first photoplethysmography signal of the subject under the irradiation of the light with the first wavelength and the second photoplethysmography signal of the subject under the irradiation of the light with the second wavelength, by using the photoelectric volume detector;

determining the concentration of the total hemoglobin specifically includes: determining the concentration $C_{tHb}$ of the total hemoglobin according to a formula as follows:

$$C_{tHb} = \frac{(\varepsilon_{RHb}^{\lambda_2} - \varepsilon_{HbO_2}^{\lambda_2})_\partial A^{\lambda_1} - (\varepsilon_{RHb}^{\lambda_1} - \varepsilon_{HbO_2}^{\lambda_1})_\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})}$$

wherein $\rho$ represents for a horizontal distance from each of a first light source configured to emit the light with the first wavelength and a second light source configured to emit the light with the second wavelength to the photoelectric volume detector, $DPF_1$ represents for the path factor corresponding to the maximum value of the photoplethysmography signal, $DPF_2$ represents for the path factor corresponding to the minimum value of the photoplethysmography signal, $DPF_1 - DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

Alternatively, in some embodiments of the present disclosure, the first absorbancy $_\partial A^{\lambda_1}$ generated when the artery of the subject pulsates under the irradiation of the light with the first wavelength $\lambda_1$ is determined according to a formula as follows:

$$_\partial A^{\lambda_1} = \ln\frac{I_{max}^{\lambda_1}}{I_{min}^{\lambda_1}}$$

wherein $I_{max}^{\lambda_1}$ represents for the maximum value of the first photoplethysmography signal, and $I_{min}^{\lambda_1}$ represents for the minimum value of the first photoplethysmography signal;

the second absorbancy $_\partial A^{\lambda_2}$ generated when the artery of the subject pulsates under the irradiation of the light with the second wavelength $\lambda_2$ is determined according to a formula as follows:

$$_\partial A^{\lambda_2} = \ln\frac{I_{max}^{\lambda_2}}{I_{min}^{\lambda_2}}$$

wherein $I_{max}^{\lambda_2}$ represents for the maximum value of the second photoplethysmography signal, and $I_{min}^{\lambda_2}$ represents for the minimum value of the second photoplethysmography signal.

Alternatively, in some embodiments of the present disclosure, determining the table of the corresponding relation between the physiological parameter and the differential path factor includes:

determining the differential path factor corresponding to each of predetermined concentrations of the total hemoglobin according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and determining the table of the corresponding relation between the physiological parameter and the differential path factor according to the physiological parameter corresponding to each of the predetermined concentrations of the total hemoglobin and the determined differential path factor.

Correspondingly, some embodiments of the present disclosure further provide a device for detecting the concentration of total hemoglobin in blood, including:

a differential path factor determination module configured to determine a differential path factor corresponding to a subject according to a physiological parameter of the subject and a predetermined table of a corresponding relation between the physiological parameter and the differential path factor, wherein the differential path factor is a difference of a path factor corresponding to a maximum value of a photoplethysmography signal and a path factor corresponding to a minimum value of the photoplethysmography signal;

an acquisition module configured to acquire a first photoplethysmography signal of the subject under an irradiation of light with a first wavelength and a second photoplethysmography signal of the subject under an irradiation of light with a second wavelength, wherein the first wavelength is different from the second wavelength; and a total hemoglobin concentration determination module configured to determine the concentration of the total hemoglobin in the blood of the subject according to the first photoplethysmography signal, the second photoplethysmography signal and the determined differential path factor.

Alternatively, in some embodiments of the present disclosure, the total hemoglobin concentration determination module is configured to determine a first absorbancy generated when an artery of the subject pulsates under the irradiation of the light with the first wavelength according to the maximum value and the minimum value of the first photoplethysmography signal, determining a second absorbancy generated when the artery of the subject pulsates under the irradiation of the light with the second wavelength according to the maximum value and the minimum value of the second photoplethysmography signal and determining the concentration of the total hemoglobin according to the first absorbancy, the second absorbancy and the determined differential path factor.

Alternatively, in some embodiments of the present disclosure the acquisition module is configured to acquire the first photoplethysmography signal of the subject under the irradiation of the light with the first wavelength and the second photoplethysmography signal of the subject under the irradiation of the light with the second wavelength by using the photoelectric volume detector;

the total hemoglobin concentration determination module is configured to determine the concentration $C_{tHb}$ of the total hemoglobin according to a formula as follows:

$$C_{tHb} = \frac{(\varepsilon_{RHb}^{\lambda_2} - \varepsilon_{HbO_2}^{\lambda_2})_\partial A^{\lambda_1} - (\varepsilon_{RHb}^{\lambda_1} - \varepsilon_{HbO_2}^{\lambda_1})_\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})}$$

wherein $\rho$ represents for a horizontal distance from each of a first light source configured to emit the light with the first wavelength and a second light source configured to emit the light with the second wavelength to the photoelectric volume detector, $DPF_1$ represents for the path factor corresponding to the maximum value of the photoplethysmography signal, $DPF_2$ represents for the path factor corresponding to the minimum value of the photoplethysmography signal, $DPF_1-DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

Alternatively, in some embodiment of the present disclosure, the total hemoglobin concentration determination module is configured to determine the first absorbancy $_\partial A^{\lambda_1}$ generated when the artery of the subject pulsates under the irradiation of the light with the first wavelength $\lambda_1$ according to a formula as follows:

$$_\partial A^{\lambda_1} = \ln\frac{I_{max}^{\lambda_1}}{I_{min}^{\lambda_1}}$$

wherein $I_{max}^{\lambda_1}$ represents for the maximum value of the first photoplethysmography signal, and $I_{min}^{\lambda_1}$ represents for the minimum value of the first photoplethysmography signal; and the total hemoglobin concentration determination module is specifically configured to determine the second absorbancy $_\partial A^{\lambda_2}$ generated when the artery of the subject pulsates under the irradiation of the light with the second wavelength $\lambda_2$ according to a formula as follows:

$$_\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, and $I_{min}^{\lambda_2}$ represents for the minimum value of the second photoplethysmography signal.

Alternatively, in some embodiments of the present disclosure, the detecting device further includes a relation table determination module configured to determine the differential path factor corresponding to each of predetermined concentrations of the total hemoglobin according to the different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and determining the table of the corresponding relation between the physiological parameter and the differential path factor according to the physiological parameter corresponding to each of the predetermined concentrations of the total hemoglobin and the determined differential path factor.

Correspondingly, some embodiments of the present disclosure further provide a nonvolatile computer readable storage medium in which a computer program is stored, and steps of the method for detecting the concentration of total hemoglobin in blood, provided by embodiments of the present disclosure, are implemented when the program is executed by a processor.

Correspondingly, some embodiments of the present disclosure further provide a device for detecting the concentration of total hemoglobin in blood including a memory, a processor and a computer program stored in the memory and capable of operating on the processor, and steps of the method for detecting the concentration of total hemoglobin in blood, provided by embodiments of the present disclosure, are implemented when the program is executed by the processor.

DETAILED DESCRIPTION OF THE EMBODIMENTS

Figure 1:
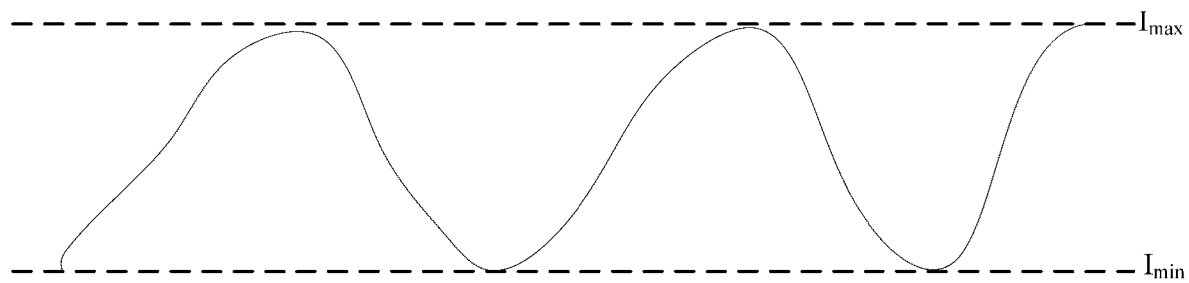
FIG. 1 is a signal schematic diagram of a PPG signal.
Figure 2:
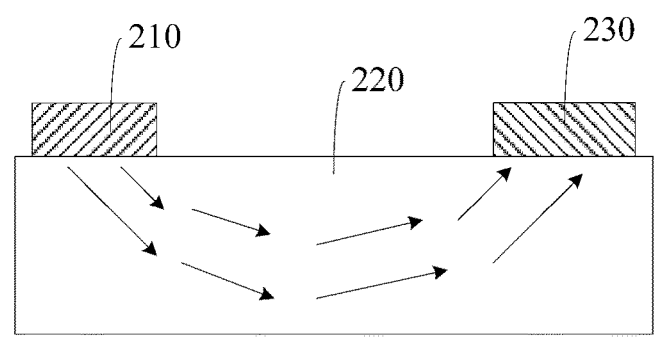
FIG. 2 is a detection schematic diagram of a PPG signal.

Blood flowing through the inside of a capillary artery, a blood capillary and a capillary vein in peripheral vessels correspondingly generates pulsatile change in a heart beating cycle. The blood volume is maximum during systole and is minimum during diastole. Thus, a PPG (Photoplethysmography) signal shown as FIG. 1 is obtained by acquiring a PPG drawing of absorption change of light in tissues of a human body by using an optical technology by virtue of a PPG. A working principle of the PPG is that as shown in FIG. 2, light with specific intensity and wavelength irradiates a skin surface 220 of a subject by a light emitting diode 210, the intensity of the light emitted after passing through the skin surface 220 is detected by using a photoelectric volume detector 230, and thus, the PPG signal in an alternating current form, shown as FIG. 1, is drawn according to the detected light intensity. The PPG signal is generated because blood is delivered to each tissues of the human body by the heart of the human body within every beating cycle and blood perfusion for blood vessels of the arteries and arterioles on the skin surface 220 on a detected position generates periodic dilation and contraction change due to the blood pumping of the heart. When the blood perfusion is increased to result in hemangiectasis due to systole, the absorbed light is increased, so that a signal received by the photoelectric volume detector 230 is weakened, or otherwise, the signal received by the photoelectric volume detector 230 is strengthened. Thus, the PPG signal has the maximum value $I_{max}$ and the minimum value $I_{min}$.

At present, a method for determining the concentration of total hemoglobin in blood by using a noninvasive method is a method for determining the concentration of total hemoglobin in blood by using the PPG signal. Optionally, an absorbancy A of the blood is determined firstly, and then, the concentration of the total hemoglobin is determined according to the absorbancy A. In addition, the absorbancy A is determined according to a formula as follows:

$$A = \log \frac{I_0}{I} = DPF * \rho \sum \varepsilon_m C_m + G;$$

wherein $I_0$ represents for the intensity of light emitted by the light emitting diode 210, I represents for the intensity of the light received by the photoelectric volume detector 230, DPF represents for a light propagation path factor, m is greater than or equal to 1 and smaller than or equal to M, m is an integer, M represents for the sum of light absorption substances, $\varepsilon_m$ represents for a light absorption coefficient of the mth light absorption substance, $C_m$ represents for the concentration of the mth light absorption substance, and G represents for attenuation caused by background absorption and scattering and is capable of representing for an absorbancy of a non-arterial component. Known according to the formula, the absorbancy A is obtained by calculating one path factor DPF. However, known from FIG. 1, the PPG signal has the maximum value $I_{max}$ and the minimum value $I_{min}$, while the path factors corresponding to $I_{max}$ and $I_{min}$ may be different, then, the absorbancy A obtained by only calculating one path factor DPF may be inaccurate, and thus, the concentration of the total hemoglobin, determined according to the absorbancy A, may also be inaccurate.

For this purpose, some embodiments of the present disclosure provide a method for detecting the concentration of total hemoglobin in blood in order to improve the accuracy of the detected concentration of the total hemoglobin in the blood.

In order to make the purpose, the technical scheme and advantages of the present disclosure clearer, the detailed description for the method and device for detecting the concentration of total hemoglobin in blood, provided by the embodiment of the present disclosure, is described below in combination with accompanying drawings. It should be understood that the preferable embodiment described as below is merely intended to describe and explain, rather than limit the present disclosure. In addition, the embodiments in this application and characteristics in embodiments may be mutually combined in the absence of conflicts. It should be noted that the size and shape of each drawing in the accompanying drawings are incapable of reflecting a true proportion and are only intended to schematically illustrate the content of the present disclosure. Moreover, same or similar symbols represent for same or similar elements or elements with the same or similar functions all the time.

Figure 3:
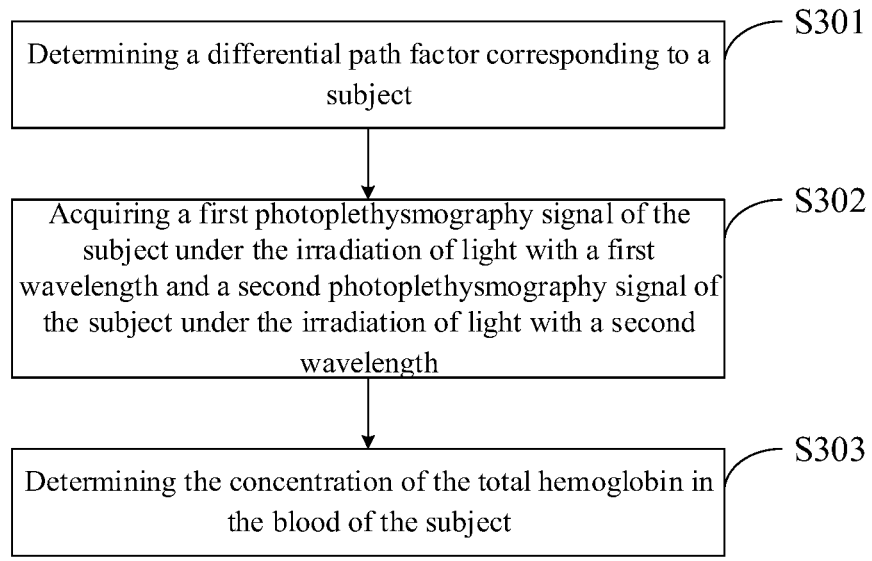
FIG. 3 is a flow diagram of a method for detecting the concentration of total hemoglobin in blood, provided by some embodiments of the present disclosure.

Some embodiments of the present disclosure provide a method for detecting the concentration of total hemoglobin in blood, as shown in FIG. 3, the detecting method may include the following steps.

S301, a differential path factor corresponding to a subject is determined according to a physiological parameter of the subject and a predetermined table of a corresponding relation between the physiological parameter and the differential path factor, wherein the differential path factor is a difference of a path factor corresponding to the maximum value of a photoplethysmography signal and a path factor corresponding to the minimum value of the photoplethysmography signal. Optionally, $DPF_1$ represents for the path factor corresponding to the maximum value $I_{max}$ of the photoplethysmography signal (namely a PPG signal), $DPF_2$ represents for the path factor corresponding to the minimum value $I_{min}$ of the photoplethysmography signal, and $DPF_1 - DPF_2$ represents for the differential path factor.

Generally, a human body may generate some physiological functions with the changes of environment and time, for example, the corresponding heart rates at different ages of a person are different, and it is also possible that the corresponding heart rates of persons with different sexes are different. Optionally, in embodiments of the present disclosure, the physiological parameter may include sex, age and heart rate. Of course, the physiological parameter may also include other representation parameters capable of representing the physiological function of the human body in an actual application, and limitations thereof are omitted herein. The physiological parameter including the sex, the age and the heart rate is only illustrated below.

Generally, the sex may be divided into male and female, the age may range from 0 to 100, and the heart rate may be 60-100 times/minute, wherein differential path factors corresponding to different sexes, different ages and different heart rates may be different, and thus, differential paths corresponding to different persons are also different. During specific implementation, the predetermined table of the corresponding relation between the physiological parameter and the differential path factor may include different physiological parameters and differential path factors corresponding to the physiological parameters one to one. For example, the physiological parameter corresponds to one differential path factor when the physiological parameter is that the sex is male, the age is 30 and the heart rate is 80 times/minute. The physiological parameter corresponds to another differential path factor when the physiological parameter is that the sex is female, the age is 30 and the heart rate is 80 times/minute. Of course, the physiological parameters of different persons may be same in an actual application, and thus, the differential path factors corresponding to the physiological parameters may also be same. In addition, the physiological parameters of the same subject are generally not changed during detection, and thus, the differential path factor of the subject during detection is constant.

S302, a first photoplethysmography signal of the subject under the irradiation of light with a first wavelength and a second photoplethysmography signal of the subject under the irradiation of light with a second wavelength are acquired, wherein the first wavelength is different from the second wavelength.

Generally, the light absorption substance in the blood under red light and infrared light wavebands is hemoglobin, therefore, the first wavelength may be set as a wavelength of the red light waveband, for example, the first wavelength may be 660 nm. Thus, the first PPG signal of the subject under the irradiation of 660 nm red light may be acquired.

The second wavelength may be set as a wavelength of the infrared light waveband, for example, the second wavelength may be 940 nm. Thus, the second PPG signal of the subject under the irradiation of 940 nm infrared light may be acquired.

S303, the concentration of the total hemoglobin in the blood of the subject is determined according to the first photoplethysmography signal, the second photoplethysmography signal and the determined differential path factor.

According to the method for detecting the concentration of total hemoglobin in blood, provided by the embodiment of the present disclosure, the differential path factor corresponding to the subject is determined according to the physiological parameter of the subject and the predetermined table of the corresponding relation between the physiological parameter and the differential path factor, so that the accuracy of the differential path factor corresponding to the subject is improved. The first photoplethysmography signal of the subject under the irradiation of the light with the first wavelength and the second photoplethysmography signal of the subject under the irradiation of the light with the second wavelength are acquired, then, the concentration of the total hemoglobin of the subject may be detected by using the noninvasive method according to the first photoplethysmography signal, the second photoplethysmography signal and the determined differential path factor with improved accuracy, and the accuracy of the obtained concentration of the total hemoglobin of the subject is improved.

During specific implementation, in embodiments of the present disclosure, the step that the concentration of the total hemoglobin in the blood of the subject is determined may optionally include:

a first absorbancy generated when the artery of the subject pulsates under the irradiation of the light with the first wavelength is determined according to the maximum value and the minimum value of the first photoplethysmography signal;

a second absorbancy generated when the artery of the subject pulsates under the irradiation of the light with the second wavelength is determined according to the maximum value and the minimum value of the second photoplethysmography signal; and the concentration of the total hemoglobin is determined according to the first absorbancy, the second absorbancy and the determined differential path factor.

Generally, the artery has a pulsation part and a static part, wherein the pulsation part of the artery may generate influences to the intensity of incident light. The PPG signal corresponding to $\lambda_i$ is detected by the photoelectric volume detector under the irradiation of light with a certain wavelength (for example, $\lambda_i$) and specific intensity, then, the absorbancy $_\partial A^{\lambda_i}$ generated when the artery of the subject pulsates may meet a formula:

$$\partial A^{\lambda_i} = A_{max}^{\lambda_i} - A_{min}^{\lambda_i} = \ln\frac{I_0^{\lambda_i}}{I_{min}^{\lambda_i}} - \ln\frac{I_0^{\lambda_i}}{I_{max}^{\lambda_i}} = \ln\frac{I_{max}^{\lambda_i}}{I_{min}^{\lambda_i}},$$

wherein $A_{max}^{\lambda_i}$ represents for the maximum absorbancy of the artery, $A_{min}^{\lambda_i}$ represents for the minimum absorbancy of the artery, $I_0^{\lambda_i}$ represents for the intensity of the incident light, $I_{min}^{\lambda_i}$ represents for the minimum value of the PPG signal detected by the photoelectric volume detector, and $I_{max}^{\lambda_i}$ represents for the maximum value of the PPG signal detected by the photoelectric volume detector.

Optionally, during specific implementation, in embodiments of the present disclosure, the first absorbancy $_\partial A^{\lambda_i}$ generated when the artery of the subject pulsates under the irradiation of the light with the first wavelength $\lambda_1$ may be determined according to a formula as follows:

$$_\partial A^{\lambda_1} = \ln\frac{I_{max}^{\lambda_1}}{I_{min}^{\lambda_1}}$$

wherein $I_{max}^{\lambda_1}$ represents for the maximum value of the first photoplethysmography signal, and $I_{min}^{\lambda_1}$ represents for the minimum value of the first photoplethysmography signal. Thus, the first absorbancy $_\partial A^{\lambda_i}$ may be obtained.

Optionally, during specific implementation, in the embodiment of the present disclosure, the second absorbancy $_\partial A^{\lambda_2}$ generated when the artery of the subject pulsates under the irradiation of the light with the second wavelength $\lambda_2$ may be determined according to a formula as follows:

$$_\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, $I_{min}^{\lambda_2}$ represents for the minimum value of the second photoplethysmography signal. Thus, the second absorbancy $_\partial A^{\lambda_2}$ may be obtained.

During specific implementation, a first light source is configured to emit the light with the first wavelength, a second light source is configured to emit the light with the second wavelength, and the photoelectric volume detector is configured to acquire the first photoplethysmography signal of the subject under the irradiation of the light with the first wavelength and the second photoplethysmography signal of the subject under the irradiation of the light with the second wavelength, wherein each of the first light source and the second light source may be a light emitting diode (LED). The structure and the function of the photoelectric volume detector may be basically the same as those in the related art and should be understood to be provided by the ordinary skilled in the art, and the descriptions thereof are omitted herein. Optionally, the horizontal distance from the first light source to the photoelectric volume detector and the horizontal distance from the second light source to the photoelectric volume detector are equal and may be preset distances or distances measured by using an instrument. In addition, the first light source and the second light source may be made to emit light by time in an actual application, so that the light emitted after the skin surface of the subject is irradiated by the first light source and the second light source may be received by the photoelectric volume detector by time, and then, the first PPG signal corresponding to the first wavelength and the second PPG signal corresponding to the second wavelength may be drawn. Although the two PPG signals including the first PPG signal and the second PPG signal may be detected by the photoelectric volume detector, the two PPG signals are detected for the same subject, $DPF_1$ corresponding to the two PPG signals are same, $DPF_2$ corresponding to the two PPG signals are also same, and furthermore, $DPF_1-DPF_2$ corresponding to the two PPG signals are still same. Thus, the step that the first photoplethysmography signal of the subject under the irradiation of the light with the first wavelength and the second photoplethysmography signal of the subject under the irradiation of the light with the second wavelength are acquired in the embodiment of the present disclosure may optionally include:

the first photoplethysmography signal and the second photoplethysmography signal which are acquired by using the photoelectric volume detector are acquired.

In embodiments of the present disclosure, the step that the concentration of the total hemoglobin is determined may optionally include: the concentration $C_{tHb}$ of the total hemoglobin is determined according to a formula as follows:

$$C_{tHb} = \frac{(\varepsilon_{RHb}^{\lambda_2} - \varepsilon_{HbO_2}^{\lambda_2})_\partial A^{\lambda_1} - (\varepsilon_{RHb}^{\lambda_1} - \varepsilon_{HbO_2}^{\lambda_1})_\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})};$$

wherein $\rho$ represents for the horizontal distance from each of the first light source and the second light source to the photoelectric volume detector, $DPF_1$ represents for the path factor corresponding to the maximum value of the photoplethysmography signal, $DPF_2$ represents for the path factor corresponding to the minimum value of the photoplethysmography signal, $DPF_1-DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

Figure 4:
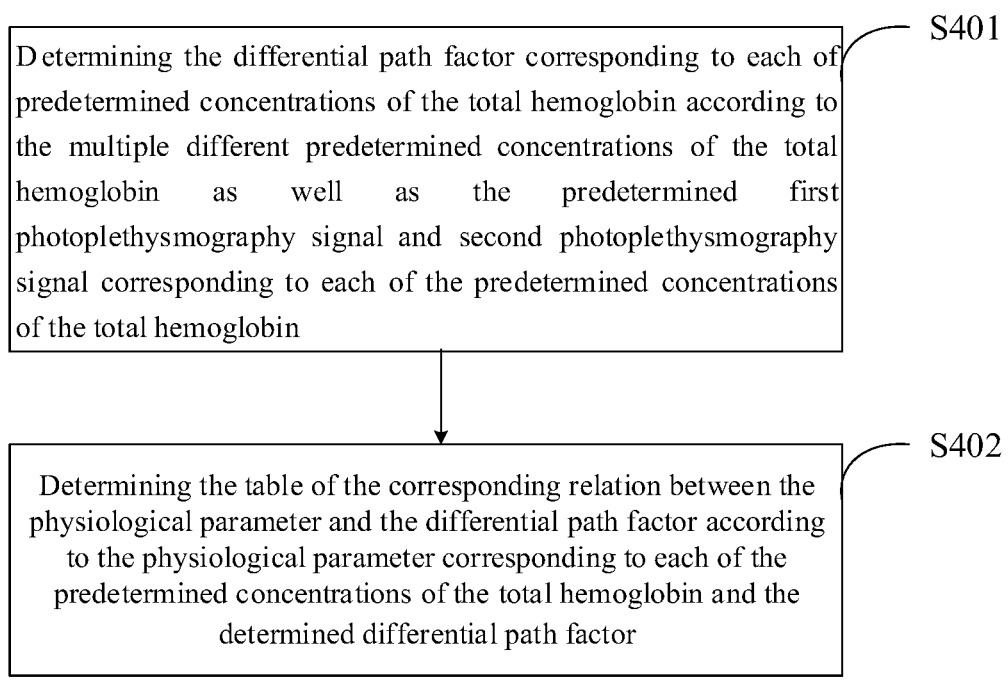
FIG. 4 is a flow diagram of a determined table of a corresponding relation between a physiological parameter and a differential path factor, provided by some embodiments of the present disclosure.

Generally, the table of the corresponding relation between the physiological parameter and the differential path factor may be determined by using various methods. During specific implementation, in embodiments of the present disclosure, the step that the table of the corresponding relation between the physiological parameter and the differential path factor is determined, as shown in FIG. 4, may include the following steps.

S401, the differential path factor corresponding to each of predetermined concentrations of the total hemoglobin is determined according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter.

Optionally, different physiological parameters may be set, then, corresponding test personnel are selected for the physiological parameters, and the blood of the selected test personnel is sampled invasively, so that blood samples corresponding to all the test personnel are acquired, next, each blood sample is measured to obtain the concentration of total hemoglobin corresponding to each of the test personnel, different concentrations of the total hemoglobin may be predetermined according to the obtained concentration of total hemoglobin corresponding to each of the test personnel and the physiological parameter corresponding to each of the test personnel, and each of the predetermined concentrations of the total hemoglobin corresponds to one physiological parameter.

In addition, the first PPG signal and the second PPG signal corresponding to each of the test personnel are detected by the photoelectric volume detector by controlling conduction of the first light source and the second light source by time. Moreover, the first absorbancy $_\partial A^{\lambda_1}$ generated when the artery of each of the test personnel pulsates under the irradiation of the light with the first wavelength $\lambda_1$ is determined according to a formula as follows:

$$\partial A^{\lambda_1} = \ln \frac{I_{max}^{\lambda_1}}{I_{min}^{\lambda_1}},$$

and the second absorbancy $_\partial A^{\lambda_2}$ generated when the artery of each of the test personnel pulsates under the irradiation of the light with the second wavelength $\lambda_2$ is determined according to a formula as follows:

$$\partial A^{\lambda_2} = \ln \frac{I_{max}^{\lambda_2}}{I_{min}^{\lambda_2}},$$

so that the differential path factor $DPF_1-DPF_2$ corresponding to the concentration of total hemoglobin corresponding to each of the test personnel is determined according to a formula $$C_{tHb} = \frac{(\varepsilon_{RHb}^{\lambda_2} - \varepsilon_{HbO_2}^{\lambda_2})\partial A^{\lambda_1} - (\varepsilon_{RHb}^{\lambda_1} - \varepsilon_{HbO_2}^{\lambda_1})\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})}.$$

S402, the table of the corresponding relation between the physiological parameter and the differential path factor is determined according to the physiological parameter corresponding to each of the predetermined concentrations of the total hemoglobin and the determined differential path factor. Optionally, each physiological parameter corresponds to one of the test personnel, and each determined differential path factor $DPF_1-DPF_2$ also corresponds to one of the test personnel, so that the table of the corresponding relation between the physiological parameter and the differential path factor may be determined by the corresponding relation to make each physiological parameter correspond to one differential path factor.

Optionally, the table of the corresponding relation between the physiological parameter and the differential path factor may be determined by establishing a neural network such as an artificial neural network (ANN) and deep neural networks (DDN). With the physiological parameter including the sex, the age and the heart rate as an example, the different physiological parameters set in the neural network are respectively shown as follows: the sex is respectively labeled as: male=man, female=woman; the age is labeled as:

$$\frac{Age}{10}$$

and is an integer, Age represents for an actual age, for example, Age=35, then, the age corresponding to 35 is labeled as 3; and the heart rate is labeled as $$\frac{Hr}{10}$$

and is an integer, Hr represents for an actual heart rate, for example, Hr=85, then, the heart rate corresponding to the heart rate 85 times/minute is labeled as 8. The sex label, the age label and the heart rate label in the physiological parameter corresponding to each of the test personnel as well as the differential path factor $DPF_1-DPF_2$ corresponding to each of the test personnel, determined according to the formula that $C_{tHb}$ meets, are used as characteristic parameters to be input into the neural network to train the neutral network, so that a mapping relation between the physiological parameter and the differential path factor, namely the table of the corresponding relation between the physiological parameter and the differential path factor, may be obtained after the training for the neutral network is completed.

Figure 5:
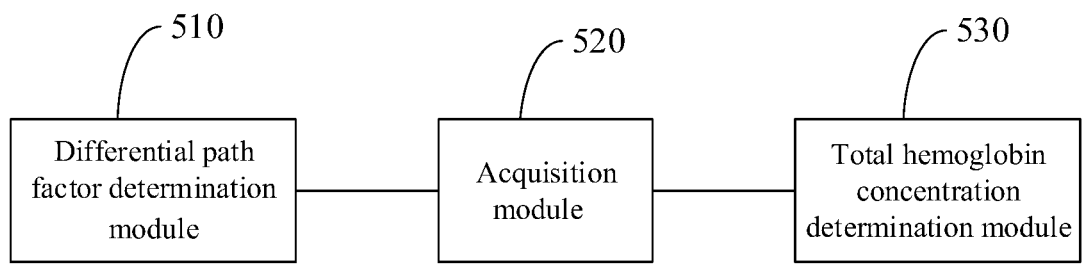
FIG. 5 is a schematic structural diagram of a device for detecting the concentration of total hemoglobin in blood, provided by some embodiments of the present disclosure.

Based on the same inventive concept, some embodiments of the present disclosure further provides a device for detecting the concentration of total hemoglobin in blood, as shown in FIG. 5, the detecting device may include:

a differential path factor determination module 510 configured to determine a differential path factor corresponding to a subject according to a physiological parameter of the subject and a predetermined table of a corresponding relation between the physiological parameter and the differential path factor, wherein the differential path factor is a difference of a path factor corresponding to the maximum value of a photoplethysmography signal and a path factor corresponding to the minimum value of the photoplethysmography signal;

an acquisition module 520 configured to acquire a first photoplethysmography signal of the subject under the irradiation of light with a first wavelength and a second photoplethysmography signal of the subject under the irradiation of light with a second wavelength, wherein the first wavelength is different from the second wavelength; and a total hemoglobin concentration determination module 530 configured to determine the concentration of the total hemoglobin in the blood of the subject according to the first photoplethysmography signal, the second photoplethysmography signal and the determined differential path factor.

During specific implementation, in the embodiment of the present disclosure, the total hemoglobin concentration determination module is optionally configured to determine a first absorbancy generated when the artery of the subject pulsates under the irradiation of the light with the first wavelength according to the maximum value and the minimum value of the first photoplethysmography signal, determining a second absorbancy generated when the artery of the subject pulsates under the irradiation of the light with the second wavelength according to the maximum value and the minimum value of the second photoplethysmography signal and determining the concentration of the total hemoglobin according to the first absorbancy, the second absorbancy and the determined differential path factor.

During specific implementation, in the embodiment of the present disclosure, the total hemoglobin concentration determination module is optionally configured to determine the first absorbancy $_\partial A^{\lambda_1}$ generated when the artery of the subject pulsates under the irradiation of the light with the first wavelength $\lambda_1$ according to a formula as follows:

$$\partial A^{\lambda_1} = \ln\frac{I_{max}^{\lambda_1}}{I_{min}^{\lambda_1}};$$

wherein $I_{max}^{\lambda_1}$ represents for the maximum value of the first photoplethysmography signal, and $I_{min}^{\lambda_1}$ represents for the minimum value of the first photoplethysmography signal; and the total hemoglobin concentration determination module is optionally configured to determine the second absorbancy $_\partial A^{\lambda_2}$ generated when the artery of the subject pulsates under the irradiation of the light with the second wavelength $\lambda 2$ according to a formula as follows:

$$\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, and $I_{min}^{\lambda_2}$ represents for the minimum value of the second photoplethysmography signal.

During specific implementation, a first light source is configured to emit the light with the first wavelength, a second light source is configured to emit the light with the second wavelength, and a photoelectric volume detector is configured to acquire the first photoplethysmography signal of the subject under the irradiation of the light with the first wavelength and the second photoplethysmography signal of the subject under the irradiation of the light with the second wavelength. Thus, the first photoplethysmography signal and the second photoplethysmography signal may be detected by only setting two light sources and one photoelectric volume detector, so that the structure of the detecting device may be simpler. Further, the acquisition module may be optionally configured to acquire the first photoplethysmography signal and the second photoplethysmography signal which are acquired by using the photoelectric volume detector in the embodiment of the present disclosure. In an actual application, the device for detecting the concentration of total hemoglobin in blood may be arranged to be independent from the first light source, the second light source and the photoelectric volume detector. Of course, the device for detecting the concentration of total hemoglobin in blood may also comprise the first light source, the second light source and the photoelectric volume detector, which is required to be designed and determined according to an actual application environment, and limitations thereof are omitted herein.

During specific implementation, in the embodiment of the present disclosure, the total hemoglobin concentration determination module is optionally configured to determine the concentration $C_{tHb}$ of the total hemoglobin according to a formula as follows:

$$C_{tHb} = \frac{(\varepsilon_{RHb}^{\lambda_2} - \varepsilon_{HbO_2}^{\lambda_2})\partial A^{\lambda_1} - (\varepsilon_{RHb}^{\lambda_1} - \varepsilon_{HbO_2}^{\lambda_1})\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})};$$

wherein $\rho$ represents for a horizontal distance from each of the first light source and the second light source to the photoelectric volume detector, $DPF_1$ represents for the path factor corresponding to the maximum value of the photoplethysmography signal, $DPF_2$ represents for the path factor corresponding to the minimum value of the photoplethysmography signal, $DPF_1-DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

During specific implementation, in embodiments of the present disclosure, the detecting device further includes a relation table determination module configured to determine the differential path factor corresponding to each of predetermined concentrations of the total hemoglobin according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and determining the table of the corresponding relation between the physiological parameter and the differential path factor according to the physiological parameter corresponding to each of the predetermined concentrations of the total hemoglobin and the determined differential path factor.

During specific implementation, in embodiments of the present disclosure may adopt a form of some embodiments in which software is completely adopted or some embodiments in which software and hardware are combined. Moreover, a form of a computer program product implemented on one or more computer usable storage media (which include, but are not limited to magnetic disk memories, optical memories and the like) containing computer usable program codes may be adopted in the present disclosure.

The problem solving theory of the device for detecting the concentration of total hemoglobin in blood is similar to that of the method for detecting the concentration of total hemoglobin in blood, so that the implementation of the device for detecting the concentration of total hemoglobin in blood may refer to that of the method for detecting the concentration of total hemoglobin in blood, and repetitions thereof omitted herein.

Based on the same inventive concept, some embodiments of the present disclosure further provide a nonvolatile computer readable storage medium in which a computer program is stored, and the steps of the method for detecting the concentration of total hemoglobin in blood, provided by embodiments of the present disclosure, are implemented when the program is executed by a processor. Optionally, the form of the computer program product implemented on one or more computer usable storage media (which include, but are not limited to magnetic disk memories, optical memories and the like) containing computer usable program codes may be adopted by the present disclosure.

Based on the same inventive concept, some embodiments of the present disclosure further provide computer equipment including a memory, a processor and a computer program stored in the memory and capable of operating on the processor, and the steps of the method for detecting the concentration of total hemoglobin in blood, provided by embodiments of the present disclosure, are implemented when the program is executed by the processor.

According to the method for detecting the concentration of total hemoglobin in blood, the device for detecting the concentration of total hemoglobin in blood, the computer readable storage medium and the computer equipment provided by the embodiment of the present disclosure, the differential path factor corresponding to the subject is determined according to the physiological parameter of the subject and the predetermined table of the corresponding relation between the physiological parameter and the differential path factor, so that the accuracy of the differential path factor corresponding to the subject is improved. The first photoplethysmography signal of the subject under the irradiation of the light with the first wavelength and the second photoplethysmography signal of the subject under the irradiation of the light with the second wavelength are acquired, then, the concentration of the total hemoglobin of the subject may be detected by using the noninvasive method according to the first photoplethysmography signal, the second photoplethysmography signal and the determined differential path factor with improved accuracy, and the accuracy of the obtained concentration of the total hemoglobin of the subject is improved.

Obviously, various alterations and modifications of the present disclosure may be made by the skilled in the art without departing from the spirit and scope of the present disclosure. Thus, the present disclosure is also intended to contain the alterations and modifications if the alterations and the modifications of the present disclosure fall into the scope of claims and equivalent technologies thereof.

The invention claimed is:

1. A method for detecting a concentration of total hemoglobin in blood, comprising:
   determining a differential path factor corresponding to a subject according to a physiological parameter of the subject and a predetermined table of a corresponding relation between the physiological parameter and the differential path factor, wherein the differential path factor is a difference of a path factor corresponding to a maximum value of a photoplethysmography signal and a path factor corresponding to a minimum value of the photoplethysmography signal;
   acquiring a first photoplethysmography signal of the subject under an irradiation of light with a first wavelength emitted by a first light source and a second photoplethysmography signal of the subject under an irradiation of light with a second wavelength emitted by a second light source, wherein the first wavelength is different from the second wavelength; and
   determining the concentration of the total hemoglobin in the blood of the subject according to the first photoplethysmography signal, the second photoplethysmography signal and the determined differential path factor;
   wherein the determining the concentration of the total hemoglobin in the blood of the subject comprises:
   determining a first absorbancy generated when an artery of the subject pulsates under the irradiation of the light with the first wavelength according to the maximum value and the minimum value of the first photoplethysmography signal;
   determining a second absorbancy generated when the artery of the subject pulsates under the irradiation of the light with the second wavelength according to the maximum value and the minimum value of the second photoplethysmography signal; and
   determining the concentration of the total hemoglobin according to the first absorbancy, the second absorbancy and the determined differential path factor;
   wherein the acquiring the first photoplethysmography signal of the subject under the irradiation of the light with the first wavelength and the second photoplethysmography signal of the subject under the irradiation of the light with the second wavelength comprises:
   acquiring the first photoplethysmography signal of the subject under the irradiation of the light with the first wavelength and the second photoplethysmography signal of the subject under the irradiation of the light with the second wavelength, by using a photoelectric volume detector;
   the determining the concentration of the total hemoglobin comprises: determining the concentration $C_{tHb}$ of the total hemoglobin according to a formula as follows:

$$C_{tHb} = \frac{(\varepsilon_{RHb}^{\lambda_2} - \varepsilon_{HbO_2}^{\lambda_2})\partial A^{\lambda_1} - (\varepsilon_{RHb}^{\lambda_1} - \varepsilon_{HbO_2}^{\lambda_1})\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})};$$

wherein $\rho$ represents for a horizontal distance from each of the first light source configured to emit the light with the first wavelength and the second light source configured to emit the light with the second wavelength to the photoelectric volume detector, $DPF_1$ represents for a path factor corresponding to the maximum value of the photoplethysmography signal, $DPF_2$ represents for a path factor corresponding to the minimum value of the photoplethysmography signal, $DPF_1$-$DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

2. The method for detecting the concentration of total hemoglobin in blood of claim 1, comprising: determining the first absorbancy $_\partial A^{\lambda_1}$ generated when the artery of the subject pulsates under the irradiation of the light with the first wavelength $\lambda_1$ according to a formula as follows:

$$_\partial A^{\lambda_1} = \ln\frac{I_{max}^{\lambda_1}}{I_{min}^{\lambda_1}};$$

wherein $I_{max}^{\lambda_1}$ represents for the maximum value of the first photoplethysmography signal, and $I_{min}^{\lambda_1}$ represents for the minimum value of the first photoplethysmography signal;

determining the second absorbancy $_\partial A^{\lambda_2}$ generated when the artery of the subject pulsates under the irradiation of the light with the second wavelength λ2 according to a formula as follows:

$$_\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, and $I_{min}^{\lambda_2}$ represents for the minimum value of the second photoplethysmography signal.

3. The method for detecting the concentration of total hemoglobin in blood of claim 1, wherein determining the table of the corresponding relation between the physiological parameter and the differential path factor comprises:
   determining the differential path factor corresponding to each of predetermined concentrations of the total hemoglobin according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and
   determining the table of the corresponding relation between the physiological parameter and the differential path factor according to the physiological parameter corresponding to each of the predetermined concentrations of the total hemoglobin and the determined differential path factor.

4. A non-transitory computer readable storage medium in which a computer program is stored, wherein steps of the method for detecting the concentration of total hemoglobin in blood of claim 1 are implemented when the program is executed by a processor.

5. A device for detecting the concentration of total hemoglobin in blood, comprising a memory, a processor and a computer program stored in the memory and capable of operating on the processor, wherein steps of the method for detecting the concentration of total hemoglobin in blood of claim 1 are implemented when the program is executed by the processor.

6. The device for detecting the concentration of total hemoglobin in blood of claim 5, wherein the processor executes the program to determine the first absorbancy $_\partial A^{\lambda_1}$ generated when the artery of the subject pulsates under the irradiation of the light with the first wavelength $\lambda_1$ according to a formula as follows:

$$_\partial A^{\lambda_1} = \ln\frac{I_{max}^{\lambda_1}}{I_{min}^{\lambda_1}};$$

wherein $I_{max}^{\lambda_1}$ represents for the maximum value of the first photoplethysmography signal, and $I_{min}^{\lambda_1}$ represents for the minimum value of the first photoplethysmography signal;
determining the second adsorbancy $_\partial A^{\lambda_2}$ generated when the artery of the subject pulsates under the irradiation of the light with the second wavelength λ2 according to a formula as follows:

$$_\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, and $I_{min}^{\lambda_2}$ represents for the minimum value of the second photoplethysmography signal.

7. The device for detecting the concentration of total hemoglobin in blood of claim 5, wherein the processor executes the program to determine the table of the corresponding relation between the physiological parameter and the differential path factor by:
   determining the differential path factor corresponding to each of predetermined concentrations of the total hemoglobin according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and
   determining the table of the corresponding relation between the physiological parameter and the differential path factor according to the physiological parameter corresponding to each of the predetermined concentrations of the total hemoglobin and the determined differential path factor.

8. A device for detecting a concentration of total hemoglobin in blood, comprising:
   a differential path factor determination module configured to determine a differential path factor corresponding to a subject according to a physiological parameter of the subject and a predetermined table of a corresponding relation between the physiological parameter and the differential path factor, wherein the differential path factor is a difference of a path factor corresponding to a maximum value of a photoplethysmography signal and a path factor corresponding to a minimum value of the photoplethysmography signal;
   an acquisition module configured to acquire a first photoplethysmography signal of the subject under the irradiation of light with a first wavelength emitted by a first light source and a second photoplethysmography signal of the subject under the irradiation of light with a second wavelength emitted by a second light source, wherein the first wavelength is different from the second wavelength; and
   a total hemoglobin concentration determination module configured to determine a concentration of the total hemoglobin in the blood of the subject according to the first photoplethysmography signal, the second photoplethysmography signal and determined differential path factor;
   wherein the total hemoglobin concentration determination module is configured to determine the concentration of the total hemoglobin by determining a first absorbancy generated when the artery of the subject pulsates under an irradiation of the light with the first wavelength according to the maximum value and the minimum value of the first photoplethysmography signal, determining a second absorbancy generated when the artery of the subject pulsates under an irradiation of the light with the second wavelength according to the maximum value and the minimum value of the second photoplethysmography signal and determining the concentration of the total hemoglobin according to the first absorbancy, the second absorbancy and the determined differential path factor;

wherein the acquisition module is configured to acquire the first photoplethysmography signal of the subject under the irradiation of the light with the first wavelength and the second photoplethysmography signal of the subject under the irradiation of the light with the second wavelength which are acquired by using the photoelectric volume detector;

the total hemoglobin concentration determination module is configured to determine the concentration $C_{tHb}$ of the total hemoglobin according to a formula as follows:

$$C_{tHb} = \frac{(\varepsilon_{RHb}^{\lambda_2} - \varepsilon_{HbO_2}^{\lambda_2})_\partial A^{\lambda_1} - (\varepsilon_{RHb}^{\lambda_1} - \varepsilon_{HbO_2}^{\lambda_1})_\partial A^{\lambda_2}}{\rho(DPF_1 - DPF_2)(\varepsilon_{RHb}^{\lambda_2}\varepsilon_{HbO_2}^{\lambda_1} - \varepsilon_{RHb}^{\lambda_1}\varepsilon_{HbO_2}^{\lambda_2})};$$

wherein $\rho$ represents for a horizontal distance from each of the first light source configured to emit the light with the first wavelength and the second light source configured to emit the light with the second wavelength to the photoelectric volume detector, $DPF_1$ represents for the path factor corresponding to the maximum value of the photoplethysmography signal, $DPF_2$ represents for the path factor corresponding to the minimum value of the photoplethysmography signal, $DPF_1$-$DPF_2$ represents for the differential path factor corresponding to the subject, $\lambda_1$ represents for the first wavelength, $\lambda_2$ represents for the second wavelength, $_\partial A^{\lambda_1}$ represents for the first absorbancy, $_\partial A^{\lambda_2}$ represents for the second absorbancy, $\varepsilon_{RHb}^{\lambda_1}$ represents for a light absorption coefficient of the light with the first wavelength corresponding to reduced hemoglobin in the artery, $\varepsilon_{RHb}^{\lambda_2}$ represents for a light absorption coefficient of the light with the second wavelength corresponding to reduced hemoglobin in the artery, $\varepsilon_{HbO_2}^{\lambda_1}$ represents for a light absorption coefficient of the light with the first wavelength corresponding to oxyhemoglobin in the artery, and $\varepsilon_{HbO_2}^{\lambda_2}$ represents for a light absorption coefficient of the light with the second wavelength corresponding to oxyhemoglobin in the artery.

9. The device for detecting the concentration of total hemoglobin in blood of claim 8, wherein the total hemoglobin concentration determination module is configured to determine the first absorbancy $_\partial A^{\lambda_1}$ generated when the artery of the subject pulsates under the irradiation of the light with the first wavelength $\lambda_1$ according to a formula as follows:

$$_\partial A^{\lambda_1} = \ln\frac{I_{max}^{\lambda_1}}{I_{min}^{\lambda_1}};$$

wherein $I_{max}^{\lambda_1}$ represents for the maximum value of the first photoplethysmography signal, $I_{min}^{\lambda_1}$ represents for the minimum value of the first photoplethysmography signal; and the total hemoglobin concentration determination module is configured to determine the second absorbancy $_\partial A^{\lambda_2}$ generated when the artery of the subject pulsates under the irradiation of the light with the second wavelength $\lambda 2$ according to a formula as follows:

$$_\partial A^{\lambda_2} = \ln\frac{I_{max}^{\lambda_2}}{I_{min}^{\lambda_2}};$$

wherein $I_{max}^{\lambda_2}$ represents for the maximum value of the second photoplethysmography signal, $I_{min}^{\lambda_2}$ represents for the minimum value of the second photoplethysmography signal.

10. The device for detecting the concentration of total hemoglobin in blood of claim 8, further comprising a relation table determination module configured to determine the differential path factor corresponding to each of predetermined concentrations of the total hemoglobin according to different predetermined concentrations of the total hemoglobin as well as the predetermined first photoplethysmography signal and second photoplethysmography signal corresponding to each of the predetermined concentrations of the total hemoglobin, wherein each of the predetermined concentrations of the total hemoglobin corresponds to one physiological parameter; and determining the table of the corresponding relation between the physiological parameter and the differential path factor according to the physiological parameter corresponding to each of the predetermined concentrations of the total hemoglobin and the determined differential path factor.

* * * * *